United States Patent [19]

Lubbers et al.

[11] 3,985,633
[45] Oct. 12, 1976

[54] DEVICE FOR THE POLAROGRAPHIC MEASUREMENT OF OXYGEN PRESSURE

[75] Inventors: Dietrich W. Lubbers, Dortmund; Albert Huch, Marbach, Marburg, both of Germany

[73] Assignee: Eschweiler & Co., Kiel, Germany

[22] Filed: Apr. 14, 1975

[21] Appl. No.: 568,111

Related U.S. Application Data

[63] Continuation of Ser. No. 414,538, Nov. 9, 1973, abandoned.

[30] Foreign Application Priority Data

Nov. 11, 1972 Germany............................ 2255382

[52] U.S. Cl. ............................... 204/195 P; 324/29
[51] Int. Cl.² ........................................ G01N 27/46
[58] Field of Search ............................. 204/195 P

[56] References Cited
UNITED STATES PATENTS

| 3,328,277 | 6/1967 | Solomons et al. | 204/195 P |
| 3,380,905 | 4/1968 | Clark | 204/195 P |
| 3,526,577 | 9/1970 | Molloy | 204/195 P |
| 3,528,403 | 9/1970 | Imredy | 204/195 P |

Primary Examiner—T. Tung
Attorney, Agent, or Firm—Michael J. Striker

[57] ABSTRACT

A platinum oxygen-pressure measuring electrode is connected with a reference electrode. An indicating device for indicating the oxygen pressure is connected with both of the electrodes, and an arrangement is interposed between the electrodes and an object to be measured and has a surface which is to be placed against the object. The arrangement offers to the diffusion of oxygen from the surface to the measuring electrode a resistance which is greater than the resistance which is offered to such diffusion of the oxygen through the object to be measured.

9 Claims, 6 Drawing Figures

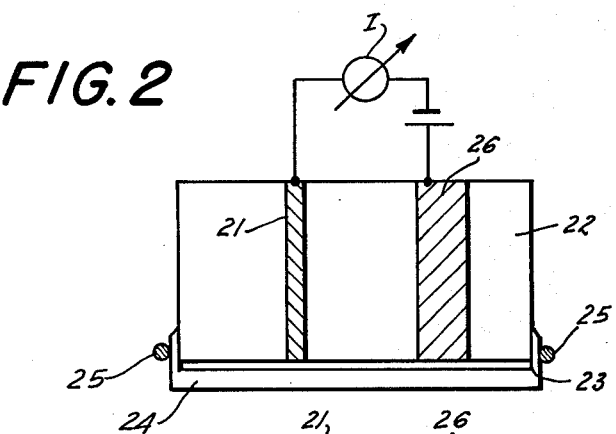
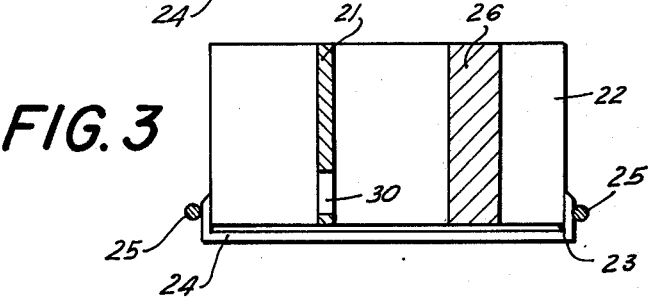
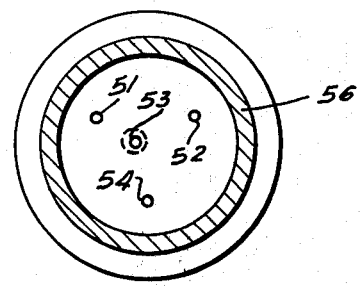
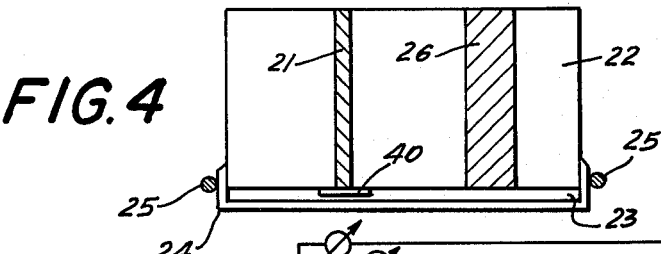
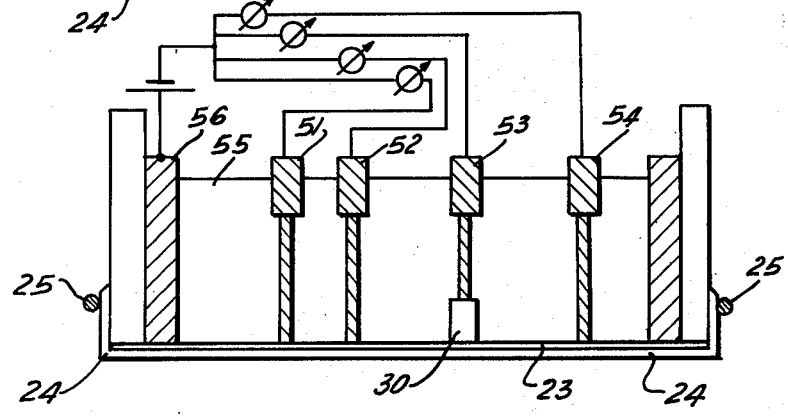

DEVICE FOR THE POLAROGRAPHIC MEASUREMENT OF OXYGEN PRESSURE

CROSS-REFERENCE TO RELATED APPLICATIONS

This application is a continuation application of our application, Ser. No. 414,538, filed on Nov. 9, 1973, now abandoned.

BACKGROUND OF THE INVENTION

The present invention relates to a device for the polarographic measurement of oxygen pressure, and in particular to such a device wherein the measuring head of the device is to be brought into mechanical contact with the object to be measured.

It is already known to provide a device of the general character with which the present invention is concerned, but a device which cannot be calibrated. This prior-art device may for instance utilize a plurality of platinum wires (Pflugers Arch, 337,185–198/1972) which are distributed over a surface area of approximately 0.5–1 $cm^2$ and are melted into a glass body acting as a carrier. There is further provided an Ag-/AgCl reference electrode which is adjacent to the platinum wires, for instance surrounding them in form of an annulus. The arrangement is in accordance with the teachings of Clark Trans. Amer. Soc. Art. Int. Org. 2,41(1956) and Luebbers Pflugers Arch 271,431/1960 and is covered with a Teflon (TM) foil which should be as thin as possible and with a cuprophane (TM) foil, which is an especially thin cellophane type foil.

It has been found that this type of device will produce reproduceable measuring results if it is carefully placed upon an object to be measured, for instance the surface of an organ of the human body. This was proven with the electrode suggested by R. Huch and disclosed on page 7 of her structural thesis delivered in 1971 in Marburg, Germany.

It is known that the calibration of oxygen electrodes requires that the measuring surface of the device is subjected to gaseous oxygen of known pressure, and that the oxygen reduction current is then measured. However, the thus obtained calibration results cannot be readily utilized for measuring the oxygen pressure in other media, for instance on the skin of a human being, because, though in this instance the reduction current will always be proportional to the oxygen quantity which reaches the measuring electrode, the relationship between reduction current and oxygen pressure is unknown because the oxygen reaches the measuring electrode only by diffusion through an unknown medium. Therefore it is necessary to keep in mind, in this context, that for purposes of calibrating the device it is the diffusion characteristics of the device alone which are of predominant importance, whereas under actual measuring conditions it is necessary to take into account both the diffusion characteristics of the device and the diffusion characteristics of the medium (i.e., object) to be measured. The term "diffusion" herein refers, of course, to the diffusion of the oxygen through the device to the measuring electrode of the latter, and through the medium whose oxygen pressure is to be measured.

Because of this second consideration, however, namely the fact that under actual measuring conditions it is necessary to also take into account the diffusion characteristic of the medium to be measured, the calibration results obtained during the previous calibration of the device cannot be used without difficulties for measuring the oxygen pressure in an actual medium, and this causes considerable difficulties in actual practice.

SUMMARY OF THE INVENTION

Accordingly, it is an object of the present invention to overcome these difficulties.

More particularly, it is an object of the invention to provide an improved device for the polarographic measurement of oxygen pressure which is not possessed of these disadvantages.

Still more particularly, it is an object of the present invention to provide such an improved device wherein the influence of the oxygen diffusion characteristics of the medium being measured upon the oxygen pressure measurements obtained with the device is eliminated.

In keeping with the above objects, and with others which will become apparent hereafter, one feature of the invention resides, in a device for the polarographic measurement of oxygen pressure, in a combination comprising a platinum oxygen-pressure measuring electrode, a reference electrode connected with the measuring electrode, and an indicating device connected with both of the electrodes for indicating the oxygen pressure determined by the same. Furthermore, we provide means for making the oxygen diffusion resistance offered by the device intermediate the surface thereof which contact the medium to be measured and the measuring electrode, greater than the oxygen diffusion resistance offered by the medium to be measured. This arrangement assures that the oxygen diffusion characteristics of the medium to be measured no longer influence the oxygen pressure measurement which is taken by the device, so that the calibration values obtained by calibrating the device can now be readily employed in conjunction with actual measurements of oxygen pressure in a medium.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 2 is a fragmentary sectioned detail view, showing an electrode arrangement according to one embodiment of the invention and provided with a relatively thick cover membrane:

FIG. 3 is a view similar to FIG. 2, illustrating an arrangement wherein the dillusion path has been lengthened;

FIG. 4 is a view similar to FIG. 3, but illustrating an electrode arrangement wherein a cover material is provided for the electrode;

FIG. 5 is a sectioned view of a further embodiment of the invention, showing a multiple electrode arrangement; and FIG. 6 is a cross-section through FIG. 5, with portions omitted for the sake of clarity.

DESCRIPTION OF THE PREFERRED EMBODIMENTS

Figure 1:
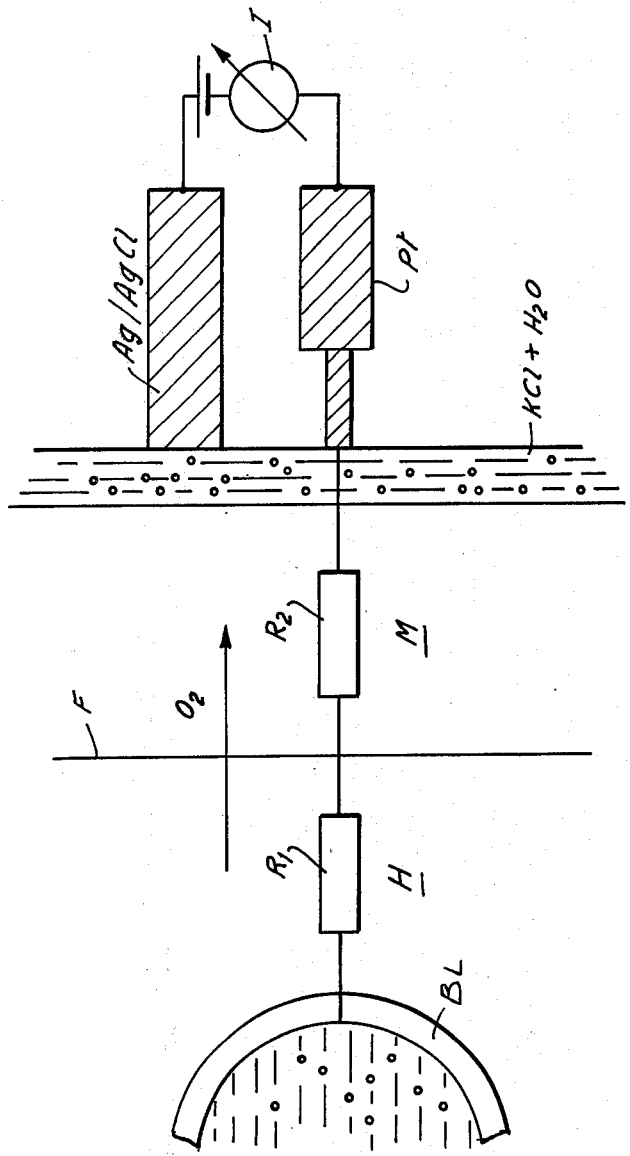
FIG. 1 is a diagrammatic illustration of a measuring diagram of a device according to the present invention when used for measuring the oxygen pressure of a medium.

FIG. 1 in the drawing is a diagrammatic illustration, showing the principle of operation of a device according to the present invention which FIG. 1 is illustrated as being used for measuring the oxygen pressure in tissue. Reference character H identifies the surface of a tissue component, that is human or animal tissue, wherein there are present blood-filled capillaries Bl of which only one is fragmentarily shown. The local oxygen pressure in the blood of the capillaries Bl is to be measured with the arrangement in FIG. 1.

The measuring device itself utilizes a diagrammatically illustrated membrane M which contacts the surface of the tissue H on the contact line or interface F. At the side of the membrane M which is removed from the interface F there is provided an electrolyte KCL+$H_2O$ with which a platinum measuring electrode Pt is connected. Also in contact with the electrolyte is a reference electrode Ag/AgCl, and an indicating instrument I is connected with both of these electrodes in the manner illustrated.

The diagrammatically shown box $R_1$ designates the resistance opposed by the tissue H to the diffusion therethrough of oxygen from the blood in the capillary Bl: similarly, $R_2$ illustrates the resistance opposed by the membrane M to the diffusion of the oxygen through this membrane. It will be seen that the membrane M separates the electrode chain Ag/AgCl—KCL $H_2O$—Pt from the tissue H.

The oxygen $O_2$ which issues from the capillary Bl and passes through the tissue H and the membrane M into the electrolyte is reduced at the electrode Pt to $$O_2 + 2e^- + 2H_2O \rightarrow H_2O + 2OH^-$$

and will disappear from the oxygen space. As a result of this, a constant stream of oxygen diffuses from Bl to the electrode Pt. Assuming that the diffusion field in one-dimensional, the oxygen pressure drop which occurs over the distance from the capillary Bl to the electrode Pt will behave in the same manner as the diffusion resistances of the diffusion path $$\frac{\Delta PO_2 \, [F-Pt]}{\Delta PO_2 \, [BLF]} \approx \frac{R_2}{R_1}$$

If $R_2 >> R_1$, then $R_2 + R_1 \approx $ 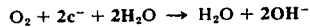 and the oxygen pressure at the surface of electrode Pt corresponds to the actual local oxygen pressure at F. Essentially the same considerations obtain if the diffusion field extends in all three coordinate directions.

If the requirement $R_2 >> R_1$ is met, the measuring device can be readily calibrated with only a very small calibrating error, in that the measuring surface of the device is exposed to a calibrating gas. Under these circumstances the calibrating values obtained with the use of calibrating gas, i.e., the calibrating curve, is valid for other media also, for instance for tissue or skin.

Coming now to a first actual embodiment of the invention, as shown in FIG. 2, it will be seen that reference numeral 21 identifies the platinum measuring electrode which is molded into a glass body 22 and connected with the indicating device 1, as is the chlorided silver electrode 26 which acts as a reference electrode. Both of these electrodes are covered with a cuprophane foil 23 acting as a barrier for the electrolyte, and with a Teflon (TM) foil or gas-diffusing membrane 24 acting as a gas trap. The foil 23 and membrane 24 are fluid-tightly retained on the body 22 by known means, for instance a ring 25 which permanently tends to contract and urges them against the surface of the body 22.

In operation of this embodiment, oxygen molecules which are on the measuring surface, the interface F of FIG. 1, diffuse into the electrolyte space where they are reduced and produce a measuring current. The diffusion resistance of the device is essentially produced in this embodiment by the Teflon membrane 24 which, if for instance measurements are to be taken on the surface of human skin, may have a thickness of at least 50 micron in order to obtain a diffusion resistance which is high relative to the diffusion resistance of the skin itself. This construction has the advantage that the device can be produced very readily, because the construction is simple and the membrane 24 is relatively thick.

The embodiment in FIG. 3 shows that an electrolyte path 30 of approximately 50–100 micron length is located ahead of the electrode 21, the term "ahead of" referring to the direction of travel of the oxygen from the interface F (see FIG. 1) to the electrode 21. This electrolyte path 30 increases the diffusion resistance of the device and permits the membrane 24 to be made thinner than in the embodiment of FIG. 2. Because of this, electrodes of different time constants must be sealed with respect to the interior by the same membrane 24, as will be discussed with reference to the embodiment in FIG. 5.

The advantage of the embodiment in FIG. 3 is that it can utilize multiple-wire electrodes wherein electrodes of different diffusion resistances can be accommodated under a single membrane which is as thin as possible, or can also be used without membranes for measurements in a KCL electrolyte.

Coming to the embodiment of FIG. 4 it will be seen that here the measuring electrodes 21 of platinum is provided with a cover 40 of a material having a low solubility coefficient for oxygen, which material serves to increase the oxygen diffusion resistance of the device. The cover 40 may, for instance, be made of Mylar (TM) and have a thickness of between substantially 5 and 10 micron, although other materials are also suitable.

The advantage of the embodiment in FIG. 4 is that the time constant is reduced, due to the fact that the diffusion path of the measuring current of oxygen molecules not only has a diffusion resistance, but that the volume in which the measured oxygen flows corresponds to a capacitance C. In an analogy to electrical current the capacitance C and the resistance R of the measuring device determine the time constant T=R × C, wherein C corresponds to the gas solubility of the material forming the diffusion path. Because $R_2$ is fixed in accordance with the present invention, time constant T can be improved only by reducing the value of C.

Under certain circumstances the measuring time in a particular measuring problem may be too long. In that case, the invention proposes to arrange one or more electrodes of a small time constant adjacent an electrode having a high diffusion resistance path. The advantage of this arrangement is that it makes it possible to measure conditions wherein the fluctuation times of the measurements are smaller than the response time of the electrode having the high diffusion resistance path. The reason for this is that the electrodes having the small time constant make it possible to determine in situ when a stationary condition of the object to be measured has occured, so that it is now possible to determine at which instance the previously calibrated electrode having the high diffusion resistance path indicates the true value of the oxygen pressure. It is, however, also possible to calibrate the electrodes having the small time constant in situ by the electrode having the high diffusion resistance if — depending upon the particular circumstances — stationary conditions of the object to be measured are achievable and can be measured with the electrode having an associated path with the high diffusion resistance.

FIG. 5 shows one embodiment in accordance with the above considerations. It uses platinum cathodic electrodes 51, 52, 53 and 54 which are imbedded in a glass body 55 together with a Ag anodic reference electrode 56. All of the electrodes are covered with a Teflon membrane 24 having a thickness of approximately 6–12 micron and with a cupraphane foil 23 serving again as the electrolyte carrier. The sealing means 25 of FIGS. 1 and 2 are again provided to seal the foil 23 and membrane 24 with respect to the glass body 55.

In this embodiment the diameter of the platinum cathodic electrodes 51–54 may be approximately 15 microns and the thickness of the Teflon membrane 24 up to approximately 20 microns. The advantage of this embodiment is that this device can be readily used for measuring the capillary oxygen pressure on the surface of the skin, because, with the dimensions given above, the amount of oxygen which is received by the device from the skin is small and does not disturb the actual diffusion conditions, thus having no influence on the accuracy of the measured results.

FIG. 6 shows that the platinum sensor elecrodes 51, 52 and 54 may be located on the corners of an equi-lateral triangle to thus define with one another a contact plane, i.e., the plane in which the device is to contact the object whose oxygen pressure is to be measured. If the contact pressure with which the device engages the object is not uniform at all of the electrodes 51, 52 and 54, then the diffusion resistance of the associated paths for the three electrodes (which is inherently the same) is no longer equal for all electrodes and a comparison of the individual measurements given by each of the three electrodes 51, 52 and 54 therefore makes it possible to determine whether the device has been properly applied to the object to be measured and is applied against this object at uniform pressure, and to make any necessary corrections. The reference electrode in this embodiment is of annular configuration, being identified with reference numeral 56 as mentioned earlier.

Approximately at the center of the triangle formed by the electrodes 51, 52 and 54 is located the fourth electrode 53. This serves as a calibrating or measuring electrode, for instance by interposing between it and the object to be measured an additional diffusion path 30 such as described with respect to the embodiment of FIG. 3. This calibrating electrode 53 will always indicate, by means of the electrically connected indicating device, the actual value of the oxygen pressure at the surface of the skin (it being assumed that this is the object to be measured) when the faster-reacting electrodes 51, 52 and 54 show constant values over longer periods of time. This makes it possible to calibrate the electrodes 51, 52 and 54 in situ, by electrode 53 and also to determine the read-out time for the calibrating electrode 53 by observing constant values for the electrodes 51, 52, 54. Each electrode type thus provides a criteria for the measurements with the respectively other type of electrode.

Evidently, the advantage of this embodiment is that by separately measuring the oxygen pressure with the electrodes 51, 52 and 54 it is possible to readily determine that the device has been applied with uniform pressure to the object being measured. It is merely necessary to assure that all three signals received by the electrically connected monitoring means from the electrodes 51, 52 and 54 are identical or react in the same manner. Moreover, this mulitple measurement of course reduces the statistical measuring error and the provision of the calibrating electrode 53 makes it possible to readily check the homogeneity of the measuring field.

If lesser requirements are made of the quality of the measuring result, then it is possible to use an electrode having a high time constant, that is a path with high resistance to oxygen diffusion, in conjunction with a single electrode having a low time constant.

It will be understood that each of the elements described above, or two or more together, may also find a useful application in other types of constructions differing from the types described above.

While the invention has been illustrated and described as embodied in a device for the polarographic measurement of oxygen pressure, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A device for the polarographic measurement of the partial pressure of oxygen in a sample, comprising an anodic reference electrode, means for positioning the device on the sample including a plurality of cathodic sensor electrodes each having oxygen-sensing end portions at spaced locations in a common plane for detecting the presence of oxygen diffused from the sample at each of said spaced locations, means for measuring the quantity of oxygen diffused from the sample including a cathodic measuring electrode having an oxygen-measuring end portion located inwardly of said plane, means for covering said electrodes including an oxygen-permeable membrane having a thickness which tends to slow the oxygen flow from the sample towards said measuring electrode so that the latter measures the partial pressure of oxygen, means connected between said anodic reference electrode and said sensor electrodes for monitoring the oxygen flow towards each of said spaced oxygen-sensing end portions so as to determine the proper application of said membrane on the sample, and means connected between said anodic reference electrode and said measuring electrode for indicating the partial pressure of oxygen in the sample.

2. A device as defined in claim 1, wherein said cathodic sensor and measuring electrodes are formed of platinum, and wherein said anodic reference electrode is annular and formed of silver-chloride coated silver.

3. A device as defined in claim 1, wherein said sensor electrodes comprise three platinum electrodes each located at the respective corners of a substantially equilateral triangle in said plane.

4. A device as defined in claim 1, wherein said oxygen-measuring end portion is located at a distance of between substantially 50 to 100 microns from said plane downstream of said oxygen flow.

5. A device as defined in claim 4, wherein said end portions of said sensor and measuring electrodes have a diameter of approximately 15 microns.

6. A device as defined in claim 1, wherein said membrane has a thickness of at least 50 microns.

7. A device as defined in claim 1, wherein said covering means further comprises an electrolyte-retaining foil positioned intermediate said membrane and said end portions of said electrodes; and wherein said membrane has a thickness of between substantialy 6 and 12 microns.

8. A device as defined in claim 7; and further comprising a glass body supporting said electrodes, and sealing means sealing said foil and said membrane with respect to said glass body.

9. A device as defined in claim 1; and further comprising a cover located intermediate said oxygen-measuring end portion and said plane, and having a low solubility coefficient for oxygen and also having a thickness of between substantially 5 and 10 microns.

* * * * *